(12) United States Patent
Jacobsen et al.

(10) Patent No.: US 6,907,799 B2
(45) Date of Patent: Jun. 21, 2005

(54) APPARATUS AND METHOD FOR NON-DESTRUCTIVE INSPECTION OF LARGE STRUCTURES

(75) Inventors: Robert A. Jacobsen, McLean, VA (US); Stuart N. Rosenwasser, Washington, DC (US); Bruce W. Bromley, Alexandria, VA (US); James L. Preston, Silver Spring, MD (US); David B. Chester, Davidsonville, MD (US)

(73) Assignee: BAE Systems Advanced Technologies, Inc., Washington, DC (US)

( * ) Notice: Subject to any disclaimer, the term of this patent is extended or adjusted under 35 U.S.C. 154(b) by 0 days.

(21) Appl. No.: 10/007,708

(22) Filed: Nov. 13, 2001

(65) Prior Publication Data

US 2003/0089183 A1 May 15, 2003

(51) Int. Cl.[7] .......................... G01M 19/00; B64F 5/00
(52) U.S. Cl. ........................ 73/865.8; 901/1; 901/44
(58) Field of Search ............................ 73/865.5, 865.8

(56) References Cited

U.S. PATENT DOCUMENTS

| | | | | |
|---|---|---|---|---|
| 3,814,211 A | * | 6/1974 | Pamer | 182/14 |
| 3,889,904 A | * | 6/1975 | Jones et al. | 244/104 R |
| 3,911,733 A | * | 10/1975 | Bhuta et al. | 73/800 |
| 4,084,427 A | * | 4/1978 | Jacoby et al. | 359/15 |
| 5,180,122 A | * | 1/1993 | Christian et al. | 244/134 F |
| 5,318,254 A | * | 6/1994 | Shaw et al. | 244/134 C |
| 5,461,473 A | | 10/1995 | Pratt et al. | 356/141.3 |
| 5,505,090 A | | 4/1996 | Webster | 73/657 |
| 5,579,102 A | | 11/1996 | Pratt et al. | 356/3.12 |
| 5,616,865 A | | 4/1997 | Webster | 73/627 |
| 5,633,707 A | * | 5/1997 | Seemann | 356/35.5 |
| 5,643,476 A | * | 7/1997 | Garmire et al. | 219/121.68 |
| 5,679,899 A | | 10/1997 | Webster et al. | 73/656 |
| 6,105,695 A | * | 8/2000 | Bar-Cohen et al. | 180/8.5 |
| 6,220,099 B1 | * | 4/2001 | Marti et al. | 73/633 |
| 6,378,387 B1 | * | 4/2002 | Froom | 73/865.8 |
| 6,477,730 B1 | * | 11/2002 | Marrero | 15/53.1 |
| 2003/0043964 A1 | * | 3/2003 | Sorenson | 378/58 |
| 2003/0048081 A1 | * | 3/2003 | Seemann | 318/68 |

* cited by examiner

Primary Examiner—Hezron Williams
Assistant Examiner—David A. Rogers
(74) Attorney, Agent, or Firm—Rossi, Kimms & McDowell LLP

(57) ABSTRACT

An automated inspection system and method enables rapid, remote and non-contact inspection of large objects, utilizing non-destructive inspection techniques, that does not require continuous manual repositioning of the inspection equipment. The inspection system includes a remote controlled robotic vehicle including a sensor package capable of non-destructive inspection of a structure and a mechanism for locating the sensor package at a plurality of inspection sights on the structure; a positioning system for determining the location of the robotic vehicle with respect to the structure to be inspected; a control system for controlling the movement of the robotic vehicle around the structure to be inspected; and an analysis systems for analyzing data generated by the sensor platform.

11 Claims, 10 Drawing Sheets

APPARATUS AND METHOD FOR NON-DESTRUCTIVE INSPECTION OF LARGE STRUCTURES

FIELD OF THE INVENTION

The invention relates in general to an apparatus and method for performing non-destructive inspection. More specifically, the invention relates to an automated method and apparatus for performing rapid, remote and non-contact inspection of large structures without requiring destruction of portions of the structure.

BACKGROUND OF THE INVENTION

A number of devices have been developed to perform non-destructive inspection of objects. For example, U.S. Pat. Nos. 5,505,090 and 5,616,865 issued to Webster, the contents of each of which are herein incorporated by reference, disclose a device for non-destructively inspecting faults in or beneath the surface of structures, such as debonds or delaminations in composite materials, cracks, broken stringers, and delaminations and the like in semi-monocoque structures. The device includes a spark gap discharge mechanism that is displaced from the object to be inspected. The spark gap discharge mechanism focuses an acoustic pulse onto a small local area of the object for vibrationally exciting the object surface. A laser Doppler camera system, also displaced from the inspection object directs a laser beam onto the excited area and derives, from the reflected light energy, the velocity of the out-of-surface displacement and relaxation frequencies generated by the surface of the excited area which are indicative of whether a fault is located in the area.

A variety of different analysis algorithms may be employed to analyze the reflected light data. U.S. Pat. No. 5,679,899 issued to Webster et al., the contents of which are herein incorporated by reference, discloses a method and apparatus for non-destructive inspection of structures that utilizes a Fast Fourier Transform (FFT) in the analysis process. The FFT is constructed for each sample point and an analysis made to set aside FFT's deviating from a pre-selected standard that represents damaged or other anomalous areas. The remaining FFT's represent an average or statistical EFT spectrum of the undamaged or fault-free area. The average FFT's and the deviating FFT's are then subtracted to provide a clear and unambiguous signal of the fault and other anomalous areas in the structure under inspection.

Each of the above-referenced patents discusses the use of an X-Y scan control system to scan the acoustic pulse generated by the spark gap across a portion of the object to be inspected. The scanning ability, however, is limited to a rather small area of the object under inspection. Accordingly, if large objects or structures are to be inspected, the device must be constantly repositioned and re-calibrated.

In view of the above, it would be beneficial if an automated device and method could be provided that would enable rapid, remote and non-contact inspection of large objects, utilizing non-destructive inspection techniques, that would not require continuous manual repositioning of the inspection equipment.

SUMMARY OF THE INVENTION

The present invention provides an automated device and method that enables rapid, remote and non-contact inspection of large objects, utilizing non-destructive inspection techniques, that does not require continuous manual repositioning of the inspection equipment. The inspection system includes a remote controlled robotic vehicle including a sensor package capable of non-destructive inspection of a structure, and a control station that provides control data to the remote controlled robotic vehicle to guide the remote controlled robotic vehicle around the structure. The robotic vehicle is capable of autonomous movement about the structure to be inspected based on data supplied by the control station.

The remote controlled vehicle preferably includes a main chassis, an extendable mast coupled to the main chassis, and an articulating arm coupled to the extendable mast. A propulsion system, for example an electric motor and battery, are provided in the main chassis. The main chassis includes various electronic control systems including a wireless communication system that enables communication between the robotic vehicle and the control station and a control processor that controls the operation of the systems of the robotic vehicle. The extendable mast includes a plurality of telescoping mast sections, wherein a first mast section is coupled to the main chassis and the articulating arm is coupled to a further mast section. The primary movement of the telescoping mast sections is preferably controlled by a motor and cable drive system, although other systems can be utilized, and the further mast section also preferable includes a fine positioning mechanism, such as a rack and pinion drive, to finely position the articulating arm. The articulating arm includes a mounting assembly that is coupled to the extendable mast, an outer tube assembly coupled to the mounting assembly at a first end, and an articulating head assembly located adjacent a second end of the outer tube assembly. The articulating head assembly includes a main body and a sensor mounting assembly coupled to the main body to which the sensor package is mounted. The articulating arm further includes an inner tube assembly coupled to a main body of the articulating head assembly, a drive shaft coupled to sensor mounting assembly, a motor for rotating the inner tube assembly, and a motor for rotating the drive shaft, wherein rotation of the inner tube assembly causes the sensor mounting assembly to rotate in a first degree of rotation and rotation of the drive shaft caused the sensor mounting assembly to rotate in a second degree of rotation.

In a preferred embodiment, the sensor package includes an acoustic pulse generator and a vibrometer, although the type of sensors utilized will depend on the particular application in which the inspection system is to be employed. The acoustic pulse generator includes a main body, first and second electrodes coupled to the main body, and a flame arrestor. The flame arrestor comprises a plurality of parallel plates and prevents propagation of flame from the spark gap in environments where fire is a consideration.

In operation, the control station prepares an inspection plan based on a digitized map of the structure to be inspected and defines a path that the robotic vehicle will travel around the structure based on the inspection plan. The control station performs analysis of data generated by the sensor package to identify anomalies in the structure being inspected.

BRIEF DESCRIPTION OF THE DRAWINGS

The invention will be described with reference to certain preferred embodiments thereof and the accompanying drawings, wherein.

DETAILED DESCRIPTION OF THE PREFERRED EMBODIMENTS OF THE INVENTION

Figure 1:
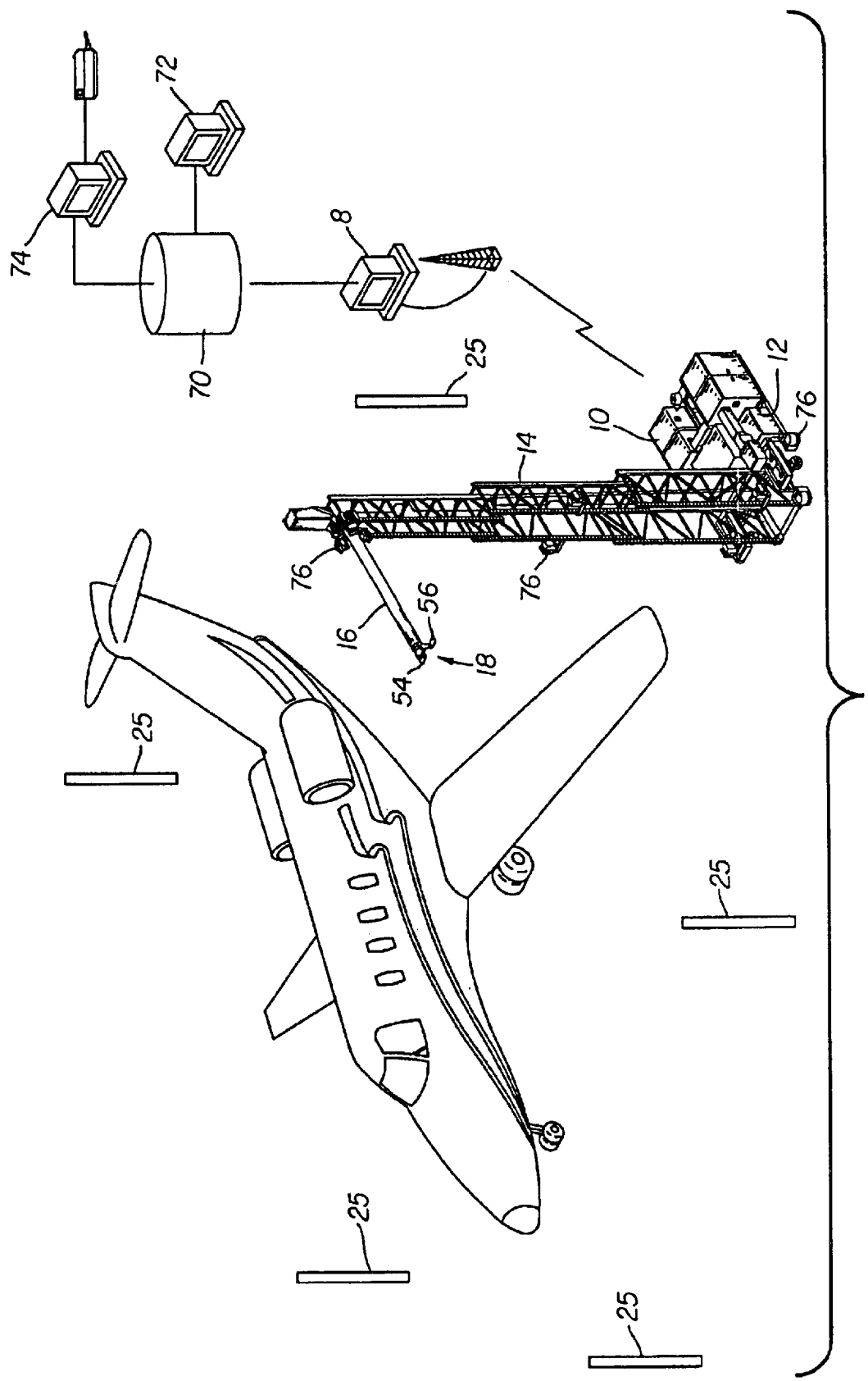
FIG. 1 illustrates an automated non-destructive inspection system in accordance with the invention.

An inspection system in accordance with the present invention is shown in FIG. 1. In the illustrated embodiment, the structure to be inspected is an aircraft, but it will be understood by those skilled in the art that the invention is applicable to any type of object or structure requiring non-destructive inspection.

As shown in FIG. 1, the inspection system includes a remotely located control station 8 and an autonomous computer controlled robotic vehicle 10. The robotic vehicle 10 includes a main chassis 12, an extendable mast 14 attached to the main chassis 12, an articulating arm 16 coupled to the extendable mast 14, and a sensor package 18 attached to the articulating arm 16. The robotic vehicle 10 is controlled to move about a structure to be inspected (the aircraft in the illustrated embodiment) based on commands received from the control station 8 via a wireless communication system. As just one example, a wireless local area network (LAN) can be provided to facilitate communication between the robotic vehicle 10 and the control station 8. Sensors within the sensor package 18 take non-destructive measurements as the robotic vehicle 10 maneuvers about the structure to be inspected.

Figure 2:
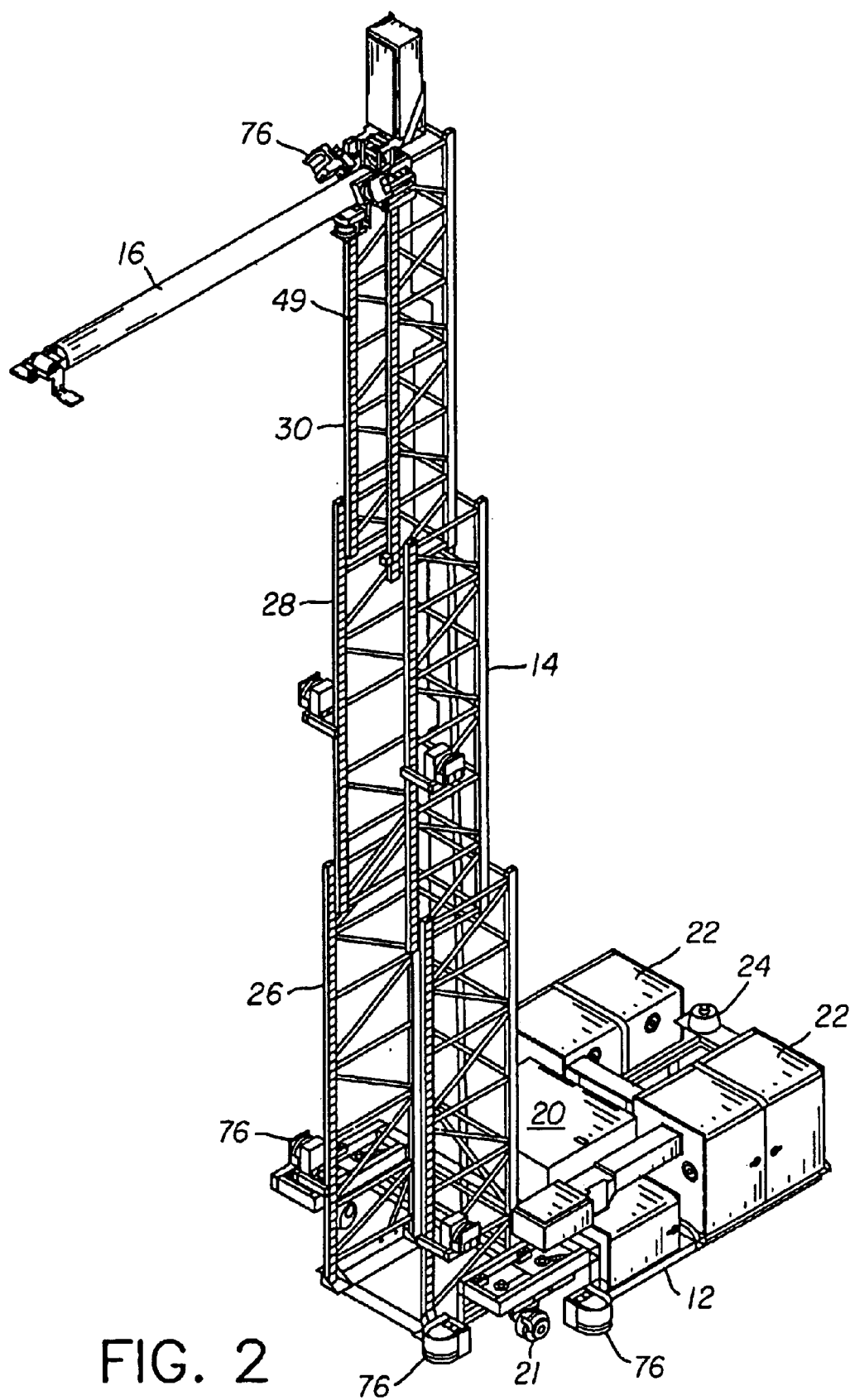
FIG. 2 is a perspective view of a robotic vehicle utilized in the inspection system illustrated in FIG. 1.

As shown in greater detail in FIG. 2, the main chassis 12 contains a propulsion system for the robotic vehicle 10 that includes a battery pack 20 and at least one electric motor driven wheel 21, electronic equipment compartments 22 to handle the electronic systems necessary to control the robotic vehicle 10 and interface with the sensor platform 18 and the control station 8, and a laser positioning head 24 that forms part of a laser guidance system that is used to identify the position and control the movements of the robotic vehicle 10. In the illustrated embodiment, the propulsion system preferably utilizes two motor driven wheels 21 and a free castor (not shown) arranged in a triangular arrangement, with the second motor driven wheel 21 being located approximately beneath the laser positioning head 24, and the batteries 20 having sufficient capacity to allow operation for at least eight hours. It should be noted, however, chat other types of propulsion systems—including propane or other types of combustion engines—could be used based on the intended application of the inspection system. The main chassis 12 has a low-slung profile, which enables the main chassis 12 to be maneuvered under portions of the structure to be inspected (for example the wings of the aircraft), thereby greatly enhancing the ability to locate the sensor package 18 adjacent to any desired location the structure. In the illustrated embodiment, the height of the main chassis 12 is preferably kept to less than one meter.

The laser positioning head 24 works in conjunction with reflector units 25 (see FIG. 1) that are located around the perimeter of the structure to be inspected. Using the laser positioning head 24 and reflectors 25, positioning measurements are taken to establish a coordinate system that defines a space in which the robotic vehicle 10 will maneuver. Either a point on the structure being inspected or a location within the perimeter defined by the reflectors 25 can be utilized as the origin of the coordinate system. A laser positioning system suitable for use in the illustrated embodiment is available from Lazerway, Inc., a subsidiary company of NDC, Ltd. Alternatively, systems such as those described in U.S. Pat. Nos. 5,461,473 and 5,579,102, the contents of which are incorporated herein by reference, may be utilized.

Figure 3:
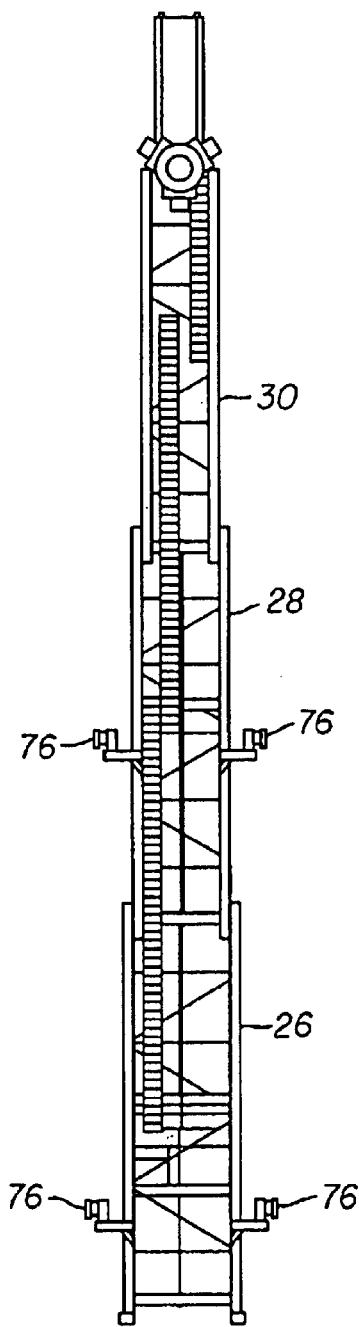
FIG. 3 is a front view of a mast structure utilized on the robotic vehicle illustrated in FIG. 2.
Figure 4:
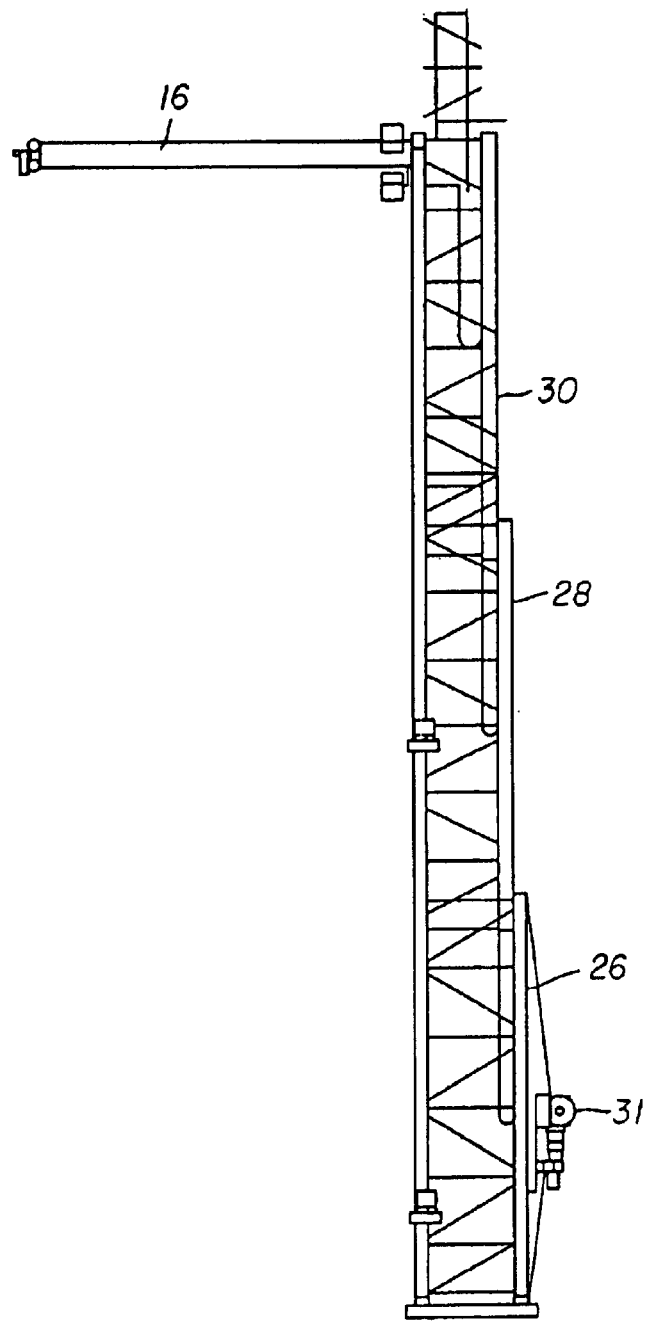
FIG. 4 is a side view of a mast structure utilized on the robotic vehicle illustrated in FIG. 2.

The structure of the extendable mast 14 is similar in concept to that of a forklift, namely, a plurality of telescoping elements are driven by a drive mechanism, for example a motor and cable system or jack screw, enabling the height of the mast 14 to be varied. In the example illustrated in FIG. 2, the extendable mast 14 includes a primary mast section 26, a secondary mast section 28 and a tertiary mast section 30. The primary mast section 26 remains fixed to the chassis 12, while the secondary mast section 28 extends from the primary mast section 26 and the tertiary mast section 30 extends from the secondary mast section 28. In the illustrated embodiment, the mast 14 preferably extends to a height of at least nine meters. Front and side views of the mast 14 are respectively illustrated in FIGS. 3 and 4. As best illustrated in FIG. 4, the movement of the primary mast section 26, the secondary mast section 28 and the tertiary mast section 30 are controlled by a motor and cable drive system 31.

Figure 5:
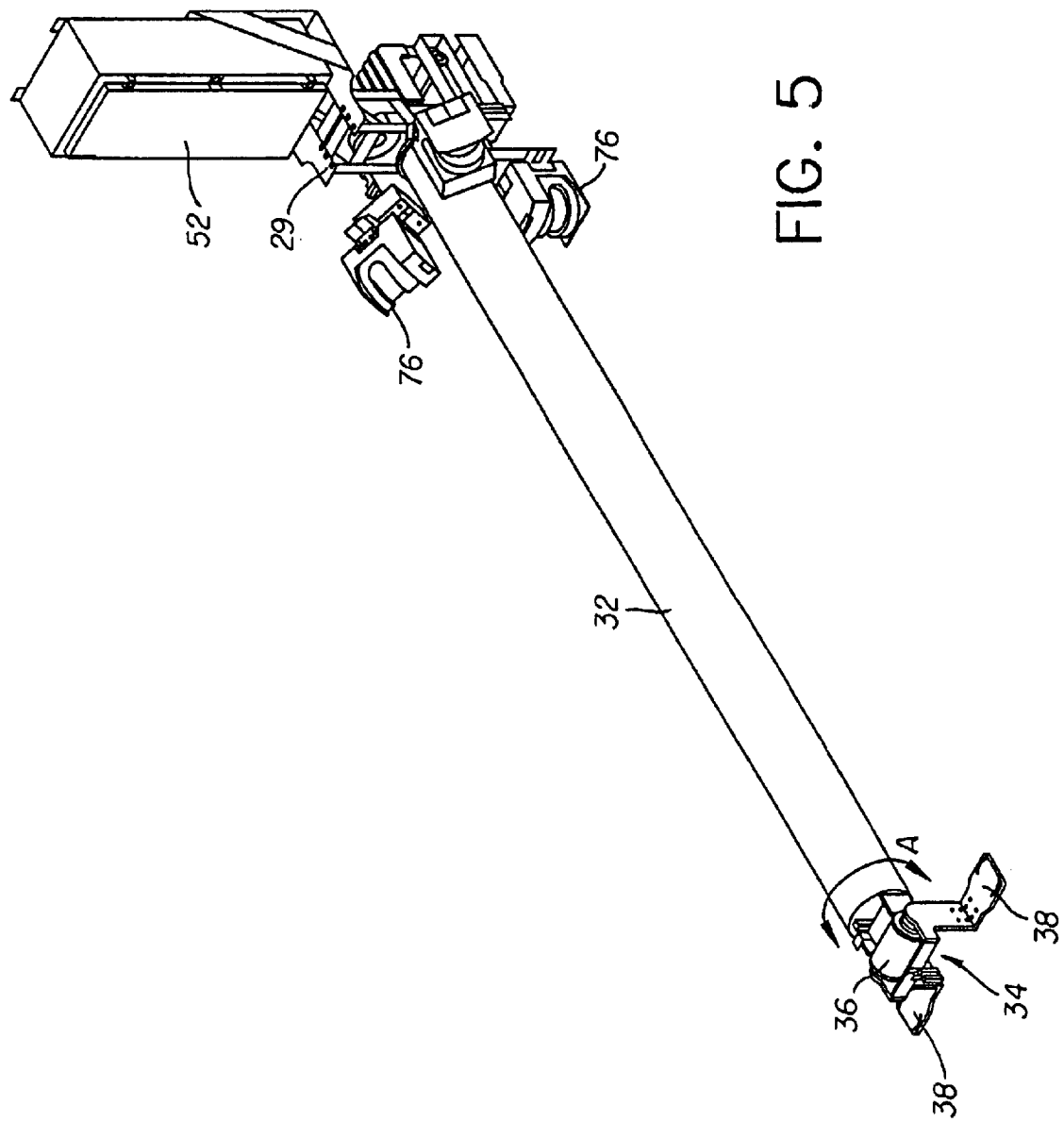
FIG. 5 is a perspective view of an articulating arm coupled to the mast structure illustrated in FIG. 4.
Figure 6:
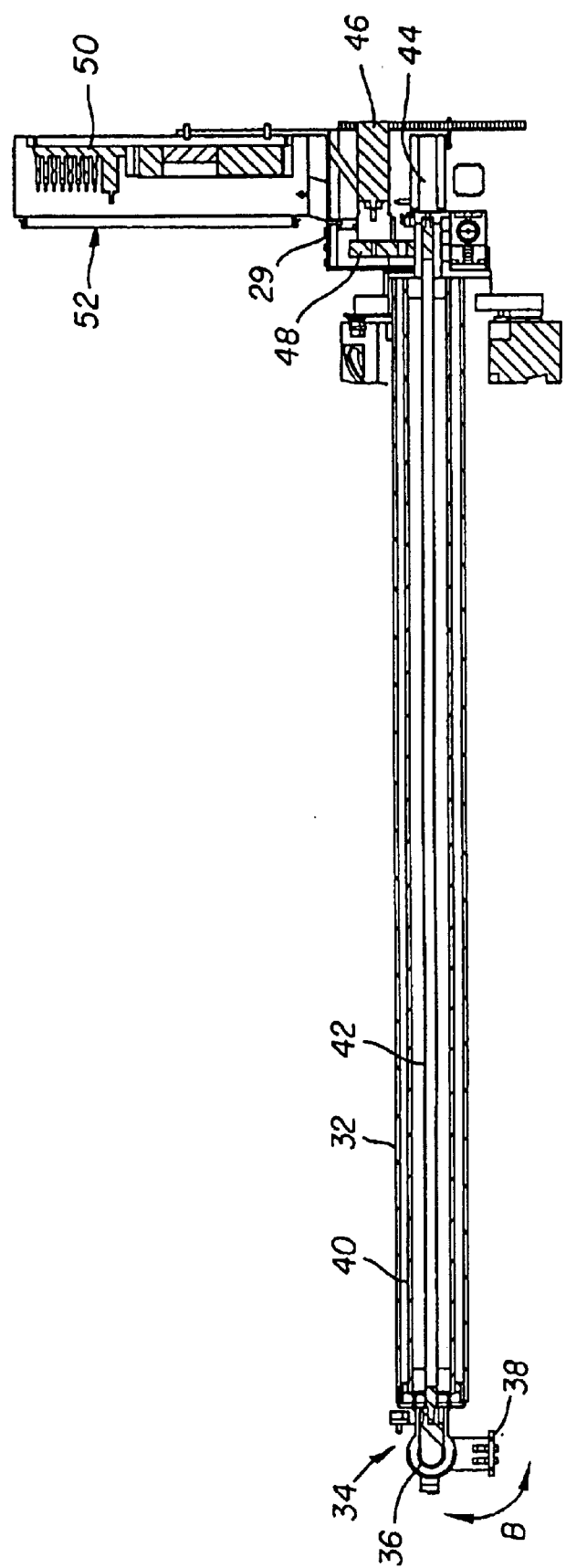
FIG. 6 is a cross-sectional view of the articulating arm illustrated in FIG. 5.

Perspective and cross-sectional views of the articulating arm 16 are respectively illustrated in FIGS. 5 and 6. As shown in FIG. 5, the articulating arm 16 includes a mounting assembly 29 to which an outer tube assembly 32 is coupled. An articulating head assembly 34 is coupled to the end of the outer tube assembly 32. The articulating head assembly 34 includes a main body 36 that contains a gearbox coupled to a sensor mounting plate assembly 38 to which the sensor package 18 (not shown) is mounted.

As shown in FIG. 6, the articulating head assembly 34 is also coupled to an inner tube assembly 40 and a drive shaft 42. The inner tube assembly 40 is provided within the outer tube assembly 32. The drive shaft 42 is provided within the inner tube assembly 40. Both the inner tube assembly 40 and the drive shaft 42 are coupled to motors that are mounted on the mounting assembly 29. A drive shaft motor 44 is used to rotate the drive shaft 42, which in is coupled to the sensor mounting plate assembly 38 in a manner to cause rotation of the sensor mounting plate assembly 38 with respect to the main body 36 of the articulating head assembly 34. An inner tube motor 46 is coupled to the inner tube assembly 40 via a drive belt assembly 48 in a manner to cause rotation of the inner tube assembly 40. As the main body 36 of the articulating head assembly 34 is fixed to the opposite end of the inner tube assembly 40, rotation of the inner tube assembly 40 by the inner tube motor 46 causes the main body 36 of the articulating head assembly 34 to rotate Accordingly, the sensor package 18 that is mounted to the sensor mounting plate assembly 38 is driven two degrees of rotation denoted by arrows A and B.

In the illustrated embodiment, the outer tube assembly 32 is used to provide structural rigidity to resist the bending force associated with the weight of the articulating head assembly 34. The inner tube assembly 40 and the drive shaft 42 are subject to a torsional forces associated with rotating the articulating head assembly 34 and driving the gearbox located in the main body 36. However, the inner tube assembly 40 and the drive shaft 42 are not required to provide structural support to oppose the bending force. Thus, the inner tube assembly 40 and the drive shaft 42 can be made of lighter weight materials, which simplifies the drive requirements for both elements.

Figure 7:
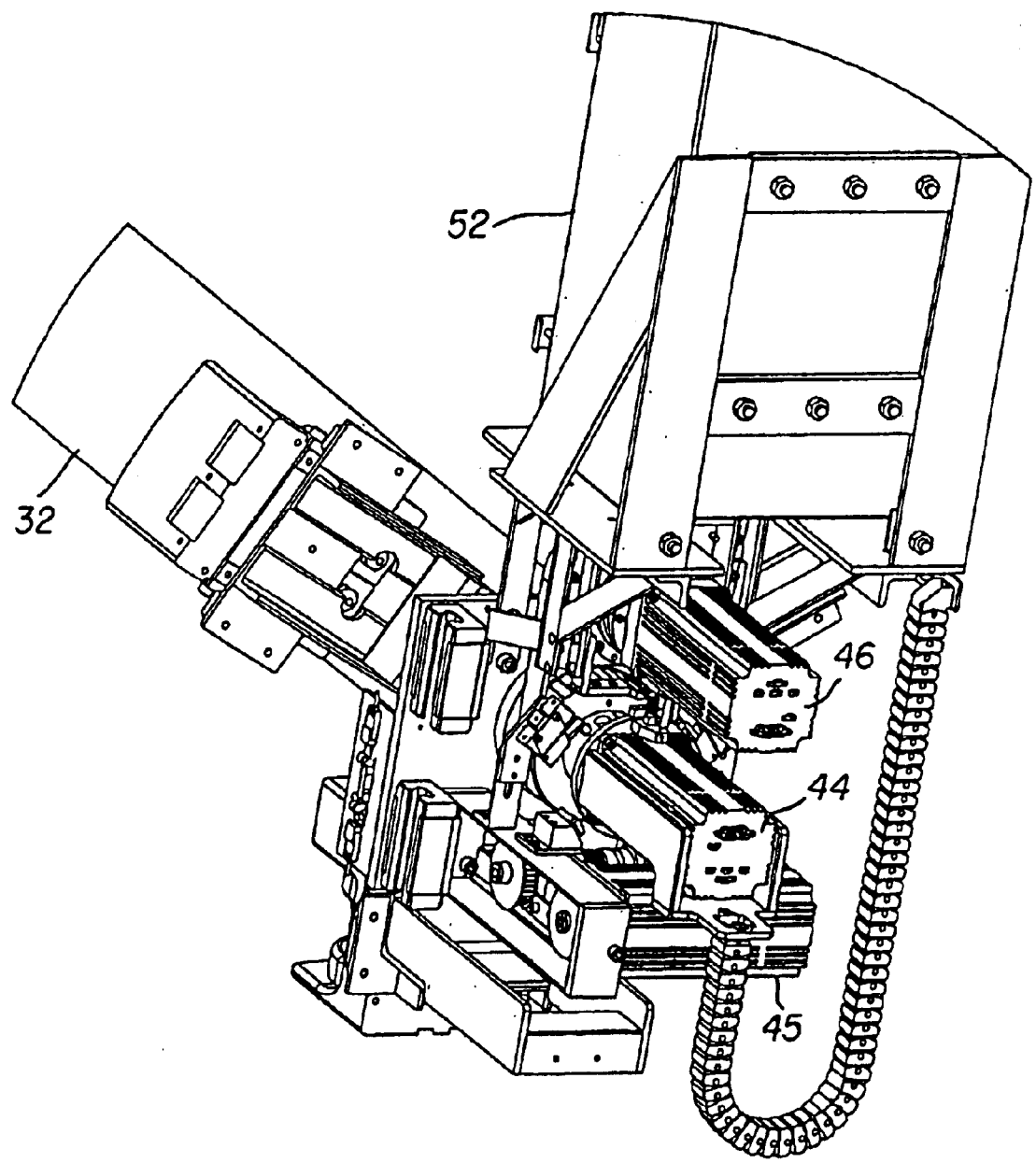
FIG. 7 is a left rear perspective view of the articulating arm illustrated in FIG. 5.
Figure 8:
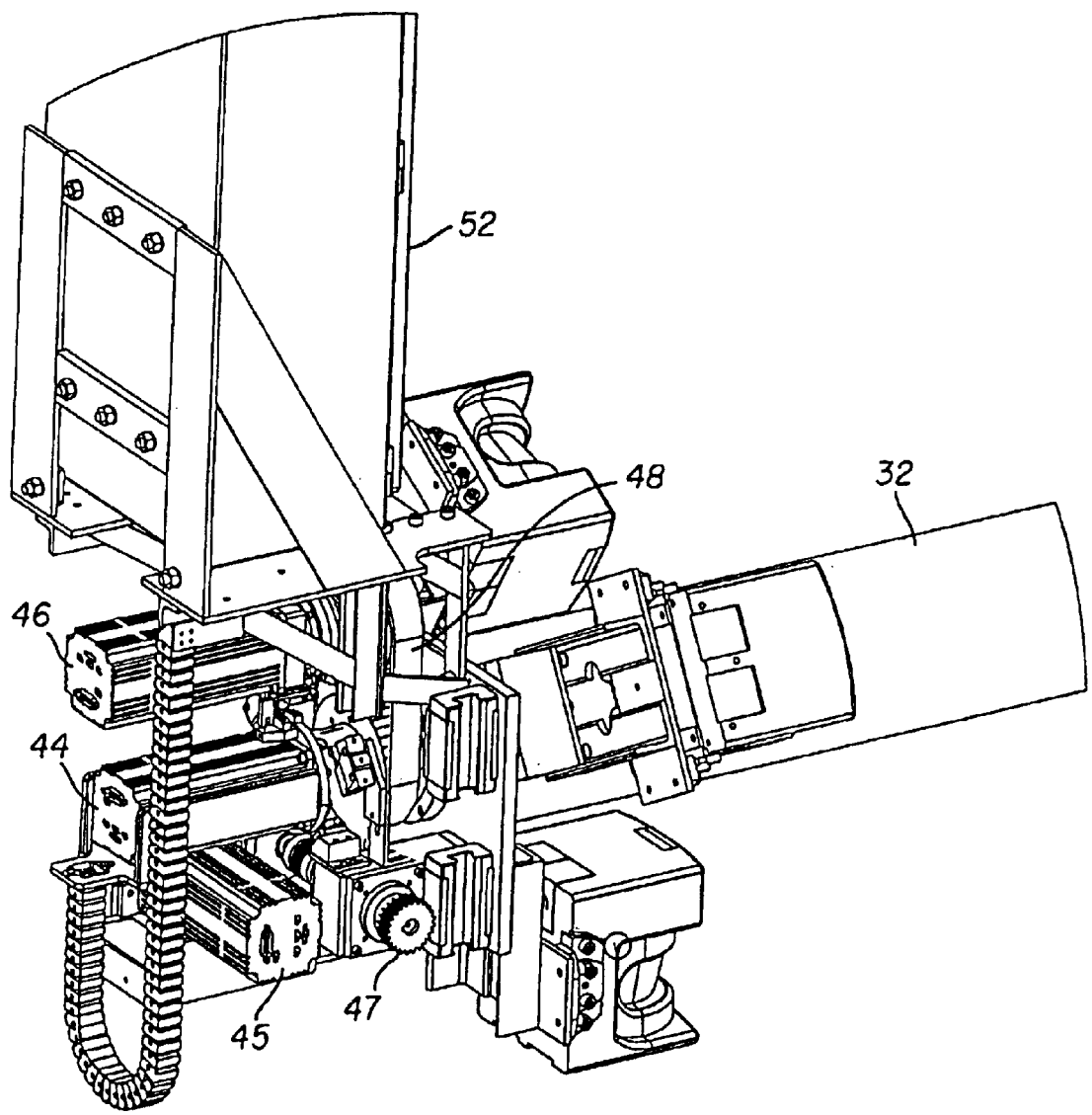
FIG. 8 is a right rear perspective view of the articulating arm illustrated in FIG. 5.

As shown in FIGS. 5 and 6, motor control circuitry 50 is located within a utility box 52 mounted on the mounting assembly 29. Additional rear perspective views illustrating the mounting of the drive shaft motor 44 and inner tube motor 46 are shown in FIGS. 7 and 8.

As previously stated, the primary positioning of the primary mast section 26, the secondary mast section 28 and the tertiary mast section 30 are controlled by the motor and cable drive system 31. However, it is preferably to provide for fine adjustment of the tertiary mast section 30. In the illustrated embodiments, fine adjustment is accomplished by a rack arid pinion drive system that includes drive motor 45, drive gears 47 (shown in FIG. 7) and racks 49 (shown in FIG. 2) provided on the tertiary mast section 30. Accordingly, fine positioning of the articulating arm 16 can be accomplished once the tertiary mast section 30 has been raised by the motor and cable drive system 31.

Referring back now to FIG. 1, in the illustrated embodiment, the sensor package 18 includes an acoustic pulse generator 54 that generates an acoustic shock wave (as opposed to a sinusoidal acoustic noise) capable of exciting a vibrational response and resonance in the structure to be inspected, and a Doppler camera system 56 that functions as a vibrometer to measure the vibrational response of the structure being inspected. The acoustic source and the Doppler camera system of the type described in U.S. Pat. Nos. 5,505,090; 5,616,865; and 5,679,899 may be utilized as the acoustic pulse generator 54 and the Doppler camera system 56. It will be understood, however, that any type of non-destructive sensor may be employed in the sensor package 18 depending on the specific application.

Figure 9:
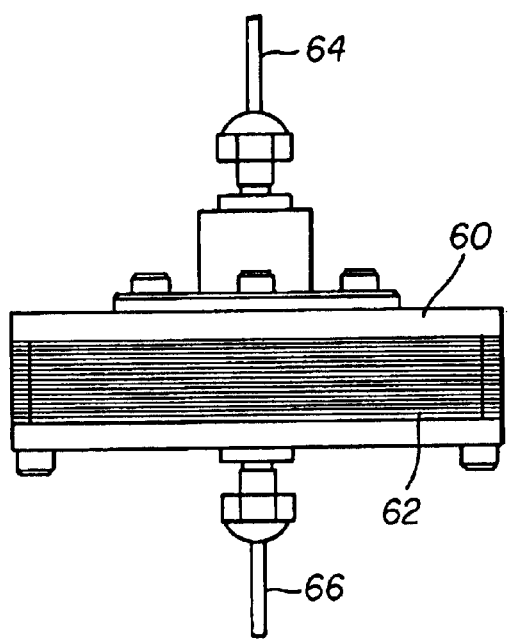
FIG. 9 is a front view of an acoustic source utilized in the system illustrated in FIG. 1.
Figure 10:
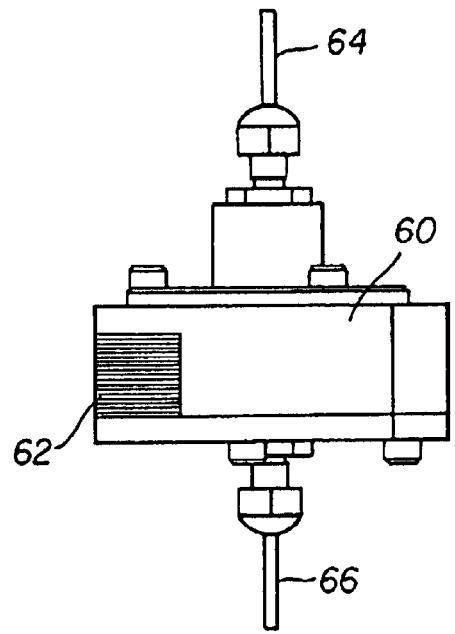
FIG. 10 is a side view of the acoustic source illustrated in FIG. 9.
Figure 11:
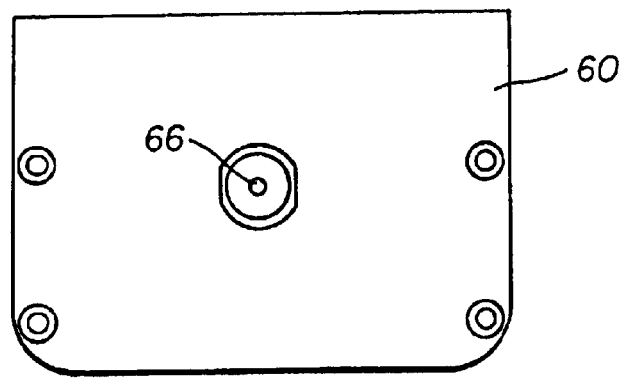
FIG. 11 is a bottom view of the acoustic source illustrated in FIG. 9.

In certain applications, for example within airplane hangers, it is desirable to provide an acoustic pulse generator 54 that can operate safely without being a possible fire ignition source. FIGS. 9, 10 and 11 respectively illustrate front, side and bottom views of a preferred acoustic pulse generator 54 that includes a main body 60, a flame arrestor structure 62, and first and second electrodes 64, 66 with associated mounting hardware. The illustrated acoustic pulse generator 54 generates an acoustic pulse by applying a voltage across a gap between the first and second electrodes 64, 66 to generate a cylindrical shaped shock. The flame arrestor structure 62 prevents the spark from having sufficient energy to ignite flammable materials that may be present.

Figure 12:
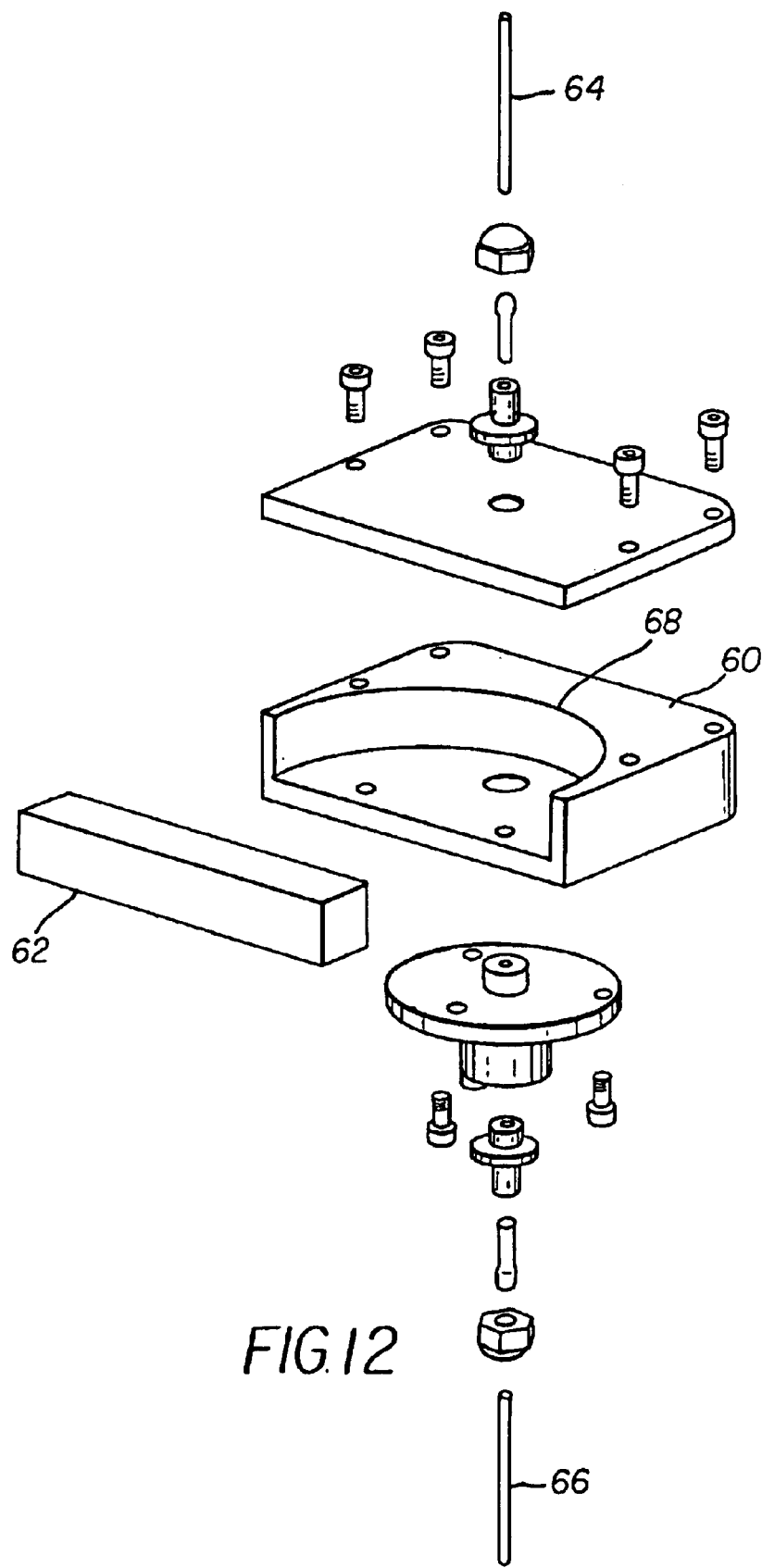
FIG. 12 is an exploded view of the acoustic source illustrated in FIG. 9.

As shown in the exploded view illustrated in FIG. 12, the main body 60 preferably includes a two dimensional parabolic reflector 68, located such that the focal point is at the location of the spark gap, which shapes and reflects the shock wave generated at the spark gap to produce a more planar wave front at the structure to be inspected, thereby enabling more simultaneous excitation over the excited area than previous acoustic sources of the type described above. The flame arrestor structure 62 is preferably made of a plurality of parallel plates, for example stainless steels, that are spaced apart and act as "Davy" plates to prevent propagation of a flame through the flame arrestor structure 62 that might ignite flammable materials in the environment around the structure to be inspected.

As described above, the control station 8 is utilized to send control signals to the robotic vehicle 10, thereby automatically maneuvering the robotic vehicle 10 around the structure to be inspected. Data generated by the sensor package 18 is passed from the robotic vehicle 10 over the wireless communication system to the control station 8. The data is then analyzed at the control station 8 to determine if fault conditions are present. Alternatively, as shown in FIG. 1, the data may be stored in a database server 70 that is capable of being accessed by other workstations to perform analysis and reporting functions. For example, an inspection work station 72 may be provided to provide inspection planning operations. Still further, actual report generation may be provided at a report generation workstation 74.

It will be understood by those skilled in the art that the architecture of the computing systems used to retrieve and analyze the data may be configured in many different configurations. For example, analysis of the data can also be performed by the on-board computer provided on the robotic vehicle 10. Regardless of the actual architecture configuration, there are two basic functional aspects to be handled, namely, control functions and data analysis functions.

Figure 13:
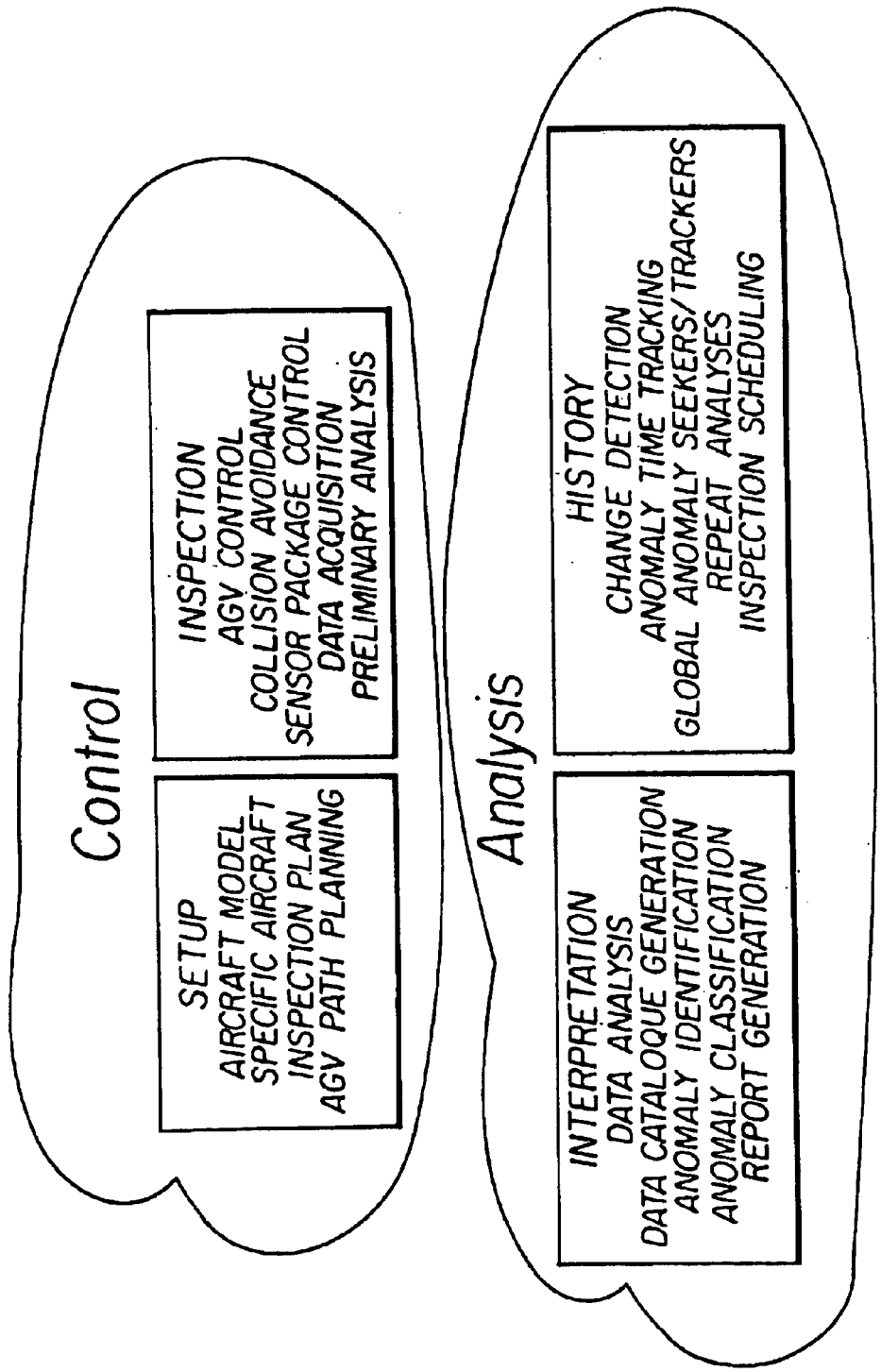
FIG. 13 is a functional diagram illustrating control functions an analysis functions to be performed by the automated inspection system illustrated in FIG. 1.

FIG. 13 is a functional diagram illustrating control functions and analysis functions to be performed by the automated inspection system. For purposes of illustration, the diagram will be discussed in connection with an aircraft inspection application of the automated inspection system. As shown in FIG. 13, the basic control functions can be divided into two basic components: a) setup control functions; and b) inspection control functions. The analysis control functions can also be divided into two basic components: a) interpretation functions; and b) history functions. Each of these functions will now be discussed in greater detail.

The setup control functions include a variety of actions that are taken to prepare for the maneuvering of the robotic vehicle 10 around the structure to be inspected. For example, in the case of aircraft inspection, a digitized map of the aircraft model to be inspected is retrieved from a database. Alternatively, if one is available, a digitized map of the specific aircraft is retrieved from a database. An inspection plan is then developed based on the digitized map of the aircraft model or specific aircraft. The inspection plan, for example, identifies a number of inspection points to be investigated on that particular model of aircraft. The number of inspection points may vary based on the age and type of aircraft involved. Once the inspection plan is developed, autonomous ground vehicle (AGV) path planning is performed. The AGV path planning determines the path which the robotic vehicle 10 will take as it is maneuvered around the aircraft to reach each of the identified inspection points. Data related to the AGV is downloaded to the robotic vehicle 10, allowing the vehicle to operate autonomously once the inspection routine begins.

The inspection functions control the actual inspection of the structure. The inspection functions include providing AGV control signals to the robotic vehicle 10. The robotic vehicle 10 may be provided with a number of different types of collision avoidance sensors, for example laser-ultrasonic, eddy current and RF non-contact type sensors, that must also be managed during the AGV process. In the illustrated embodiment, for example, a plurality of laser-ultrasonic sensors 76 (Sick, AG PLS-101-312) are located at various points on the robotic vehicle 10 including around the base of the vehicle, on the extendable mast 14 and on the articulating arm 16. The sensors 76 provide collision signals when objects appear in the path of the vehicle. Accordingly, managing collision avoidance is also an inspection control function. In addition, data acquisition is performed based on the data generated by the sensor package 18. If desired, preliminary analysis of the data is also performed.

The interpretations functions are utilized to perform interpretation and analysis of data to determine if faults are present within the structure being inspected. The interpretation functions include data analysis, data catalogue generation, anomaly identification, anomaly classification and report generation. As stated above, a variety of algorithms may be utilized to perform the data analysis, as well as the anomaly detection and classification. In the case of the use of acoustic vibration signals (surface velocity vs. time) discussed above, time and frequency domain based signal processing algorithms are used to identify, classify, size and locate anomalies without operator intervention.

The history functions include tracking changes, anomaly time tracking, repeat analysis and inspection scheduling. It is preferably, for example in the case of aircraft, that a complete data file be maintained for a particular structure showing the location and extent of any detected anomalies. The data file can then be used to compare results of the course of time to determine degradation factors for the structure.

The disclosed inspection system allows the definition of a three-dimensional model of the space in which the robotic vehicle 10 is to operate. Based on the three-dimensional model, an autonomous inspection routine is developed to allow autonomous movement of the robotic vehicle 10 to the various inspection points on the structure of interest. Collision avoidance sensors prevent the robotic vehicle 10 from contacting the structure itself or any other objects that may come into the path of the robotic vehicle 10 during the inspection process. Data from the non-destructive sensors provided in the sensor package 18 can be stored in a hierarchical database related to the structure of interest. Accordingly, the disclosed inspection system provides a number of advantages over the conventional manual process of taking measurements at various inspection points.

The invention has been described with reference to certain preferred embodiments thereof. It will be understood, however, that modifications and variations are possible within the scope of the appended claims. For example, although completely autonomous operation is preferred, the robotic vehicle 10 can be alternatively manually maneuvered to each inspection point utilizing a joystick operator input provided at the control station 8.

What is claimed is:

1. An inspection system comprising:
   an autonomous remote controlled robotic vehicle including a sensor package for non-destructive inspection of a structure; and
   a control station that provides control data to the remote controlled robotic vehicle to guide the remote controlled robotic vehicle around the structure, wherein the control data is based on a three dimensional model of a space in which the remote controlled robotic vehicle is to operate and in which the structure is located;
   wherein the vehicle includes a low profile main chassis for maneuvering under portions of the structure to be inspected, an extendable mast fixedly coupled to the main chassis, the extendable mast being extendable substantially perpendicularly to the main chassis, and an articulating arm coupled to the mast; and
   wherein the main chassis includes a propulsion system.

2. An inspection system as claimed in claim 1, wherein the propulsion system includes at least one electric motor and a battery.

3. An inspection system as claimed in claim 1, wherein the main chassis includes electronic control systems including a wireless communication system that enables communications between the robotic vehicle and the control station.

4. An inspection system as claimed in claim 1, wherein the robotic vehicle includes a plurality of collision avoidance sensors.

5. An inspection system as claimed in claim 1, wherein the control station prepares an inspection plan based on a digitized map of the structure to be inspected and defines a path that the robotic vehicle will travel around the structure based on the inspection plan.

6. An inspection system as claimed in claim 1, wherein the control station performs analysis of data generated by the sensor package to identify anomalies in the structure being inspected.

7. An inspection system according to claim 1, wherein the height of the chassis is less than one meter.

8. An inspection system according to claim 7, wherein the vehicle includes two motor driven wheels and a free castor arranged in a triangular arrangement.

9. An inspection, system as claimed in claim 1, wherein the sensor package includes an acoustic pulse generator and a vibrometer.

10. An inspection system as claimed in claim 9, wherein the acoustic pulse generator includes a main body, first and second electrodes coupled to the main body, and a flame arrestor.

11. An inspection system as claimed in claim 10, wherein the flame arrestor comprises a plurality of parallel plates.

* * * * *